United States Patent [19]

Nesvadba

[11] Patent Number: 5,280,057
[45] Date of Patent: Jan. 18, 1994

[54] CYCLOALKYLIDENE BISPHENOL PHOSPHITES

[75] Inventor: Peter Nesvadba, Marly, Switzerland

[73] Assignee: Ciba-Geigy Corporation, Ardsley, N.Y.

[21] Appl. No.: 4,147

[22] Filed: Jan. 13, 1993

[30] Foreign Application Priority Data

Jan. 21, 1992 [CH] Switzerland .................. 149/92

[51] Int. Cl.$^5$ ............... C08K 5/527; C07F 9/6574
[52] U.S. Cl. ....................... 524/119; 558/78
[58] Field of Search .............. 524/119, 326; 558/78

[56] References Cited

U.S. PATENT DOCUMENTS

| | | | |
|---|---|---|---|
| 2,883,365 | 4/1959 | Mathes | 524/326 |
| 2,894,004 | 7/1959 | Dietzler | 524/326 |
| 3,441,633 | 4/1969 | Friedman | 524/119 |
| 3,467,733 | 9/1969 | Dever et al. | 558/78 |
| 3,491,157 | 1/1970 | Deitzler et al. | 524/326 |
| 3,655,832 | 4/1972 | Kauder et al. | 558/78 |
| 3,856,728 | 12/1974 | Abramoff . | |
| 4,206,111 | 6/1980 | Valdiserri et al. | 524/91 |
| 4,312,803 | 1/1982 | Markezich et al. . | |
| 4,325,863 | 4/1982 | Hinsken et al. . | |
| 4,338,244 | 7/1982 | Hinsken et al. . | |
| 4,463,112 | 7/1984 | Leistner et al. | 524/120 |

FOREIGN PATENT DOCUMENTS

| | | |
|---|---|---|
| 0033395 | 8/1981 | European Pat. Off. . |
| 1237312 | 6/1967 | Fed. Rep. of Germany . |
| 1384809 | 11/1963 | France . |
| 934988 | 8/1963 | United Kingdom . |

OTHER PUBLICATIONS

C.A. vol. 62, 9061h (1965).
(Houben-Weyl) Methoden der organischen Chemie (1964).
(Houben-Weyl) Methoden der organischen Chemie (1976).

Primary Examiner—Veronica P. Hoke
Attorney, Agent, or Firm—Luther A. R. Hall

[57] ABSTRACT

There are disclosed novel compounds of formula I

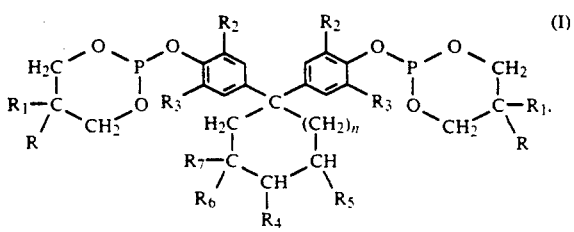

wherein n is 0, 1 or 2,

R and $R_1$ are each independently of the other $C_1$-$C_4$alkyl or, when taken together, are a 2,3-dehydropentamethylene radical, $R_2$ is $C_1$-$C_4$alkyl or $C_5$-$C_6$cycloalkyl, and $R_3$ is hydrogen, $C_1$-$C_4$alkyl or $C_5$-$C_6$cycloalkyl, $R_4$, $R_5$, $R_6$ and $R_7$, if n=1, are each independently of one another hydrogen or $C_1$-$C_4$alkyl, or, if n=0 and if n=2, are hydrogen, as stabilisers for protecting organic materials against thermal, oxidative or light-induced degradation.

17 Claims, No Drawings

CYCLOALKYLIDENE BISPHENOL PHOSPHITES

The present invention relates to novel phosphites, to compositions comprising them, to their use as stabilisers and to a process for their preparation.

Spiro-linked biphosphites that are used as stabilisers for polyolefins are disclosed in DE-B-1 237 312 and in U.S. Pat. No. 4,206,111. In addition to a great number of other phosphites, EP-A-33 395 and U.S. Pat. No. 4,463,112 also embrace generically bisphenol phosphites in which the phosphorous acid is esterified with monofunctional alcohols. Bisphosphites of the type

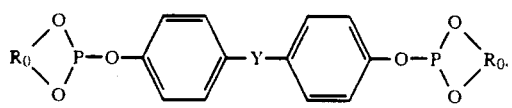

wherein Y contains a heteroatom, are embraced by U.S. Pat. No. 3,856,728.

There is still a need to provide effective stabilisers for organic materials which are susceptible to oxidative, thermal or light-induced degradation.

Accordingly, the invention relates to compounds of formula I

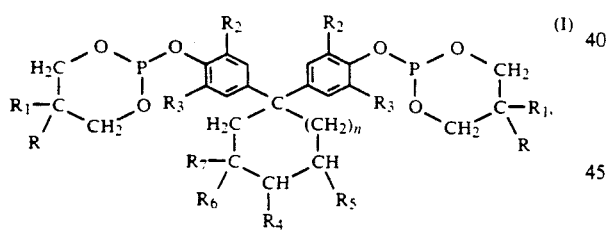

wherein
n is 0, 1 or 2,
R and $R_1$ are each independently of the other $C_1$-$C_4$alkyl or, when taken together, are a 2,3-dehydropentamethylene radical,
$R_2$ $C_1$-$C_4$alkyl or $C_5$-$C_6$cycloalkyl,
$R_3$ is hydrogen, $C_1$-$C_4$alkyl or $C_5$-$C_6$cycloalkyl, and
$R_4$, $R_5$, $R_6$ and $R_7$, if n=1, are each independently of one another hydrogen or $C_1$-$C_4$alkyl, or, if n=0 and if n=2, are hydrogen.

Compounds of formula I, wherein n is 1 or 2, are preferred.

Preferred compounds of formula I are also those wherein $R_2$ is $C_1$-$C_4$alkyl or cyclohexyl $R_3$ is hydrogen, $C_1$-$C_4$alkyl or cyclohexyl.

Particularly interesting compounds of formula I are those in which n=1. Among them, those compounds merit special interest wherein $R_4$ is hydrogen and $R_5$, $R_6$ and $R_7$ are each independently of one another hydrogen or methyl.

Further interesting compounds of formula I are those wherein $R_2$ is methyl, butyl or cyclohexyl $R_3$ is hydrogen, methyl, butyl or cyclohexyl. Of particular interest are those compounds of formula I, wherein $R_2$ is methyl or tert-butyl $R_3$ is hydrogen, methyl or tert-butyl.

Also preferred are compounds of formula I, wherein $R_5$, $R_6$ and $R_7$ are hydrogen and $R_4$ is hydrogen or tert-butyl, more particularly those wherein $R_4$, $R_5$, $R_6$ and $R_7$ are hydrogen.

Especially preferred are also compounds of formula I, wherein R and $R_1$ are each independently of the other methyl or butyl or, when taken together, are a 2,3-dehydropentamethylene radical.

If n=0, novel cyclopentyl compounds of formula

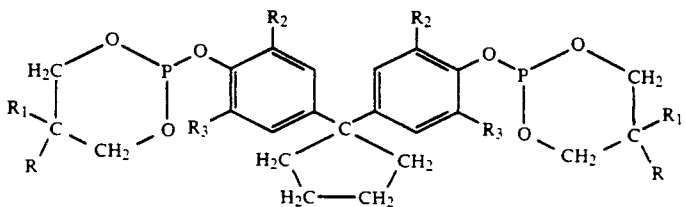

are obtained. If n=2 or n=1, corresponding cycloheptyl or unsubstituted or substituted cyclohexyl compounds are obtained.

R, $R_1$, $R_2$, $R_3$, $R_4$, $R_5$, $R_6$ and $R_7$ as $C_1$-$C_4$alkyl can be linear or branched and are methyl, ethyl, 1-propyl (n-propyl), 2-propyl (isopropyl), 1-butyl (n-butyl), 2-butyl (sec-butyl), 2-methylpropyl (isobutyl) or 1,1-dimethylethyl (tert-butyl).

The compounds of formula I may conveniently be prepared by reacting a compound of formula II

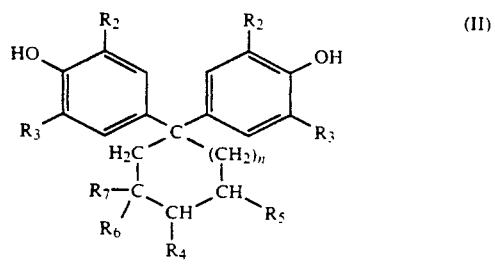

with a suitable halophosphite of formula III

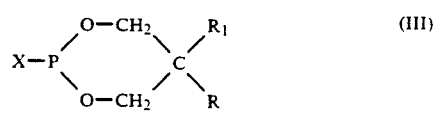

wherein X is a chlorine, bromine or iodine atom, preferably a chlorine atom. The substituents R, $R_1$, $R_2$, $R_3$, $R_4$, $R_5$, $R_6$ and $R_7$ the index n are as defined above for formula I.

The invention therefore also relates to a process for the preparation of compounds of formula I, which comprises reacting a compound of formula II with a cyclic halophosphite of formula III.

A preferred process is one wherein the cyclic halophosphite of formula III is a chlorophosphite of formula IIIa

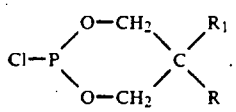

(IIIa)

A particularly preferred process comprises carrying out the reaction in the presence of a base. Suitable organic bases include organic amines (e.g. trimethylamine, triethylamine, tributylamine, N,N-dimethylaniline, N,N-diethylaniline or pyridine), hydrides (e.g. lithium, sodium or potassium hydride), organometal compounds (e.g. methyl lithium, butyl lithium) or alcoholates (e.g. sodium methylate). Suitable inorganic bases are typically alkali metal hydroxides such as sodium hydroxide or potassium hydroxide, or alkali metal carbonates such as sodium or potassium carbonate. It is especially convenient to use triethylamine or butyl lithium as base.

The reaction is conveniently carried out in a solvent, starting from one of the educts, preferably the bisphenol of formula II, and with or without the base.

Suitable solvents are aliphatic and aromatic hydrocarbons or aliphatic and aromatic halogenated hydrocarbons or ethers. Suitable aromatic hydrocarbons are typically benzene, toluene and xylene, and a chlorinated aromatic hydrocarbon may be chlorobenzene. Suitable halogenated aliphatic hydrocarbons are typically methylene chloride or chloroform. Suitable ethers are typically diethyl ether, dibutyl ether or tetrahydrofuran. Preferred solvents are aromatic hydrocarbons, in particular toluene or xylene.

The reaction is carried out conveniently by slowly adding the second educt, preferably the cyclic halophosphite of formula III, with cooling and mixing. The temperature is not critical. It is desirable to keep the mixture, with stirring, at a temperature in the range from $-30°$ C. to $+50°$ C., typically from $0°$ C. to $20°$ C. and, preferably, from $5°$ C. to $15°$ C. A precipitate of the hydrochloride of the base is conveniently removed by filtration.

The educts are preferably added in the ratio of 1 mol of the compound of formula II to 2 mol of the compound of formula III. It is, however, also possible to use an excess of the compound of formula III, typically 2.01 to 2.2 equivalents. The amount in which the base is added may vary from the catalytic through the stoichiometric amount up to a multiple of the molar excess over the amount of compound of formula III. It is preferred to add the base in equimolar amount with respect to the compound of formula III.

The compound of formula I can be isolated from the reaction mixture by conventional working up methods, conveniently by concentration, taking up in a solvent, removing insoluble matter by filtration, crystallisation and drying. Dissolving and filtration can be carried out at temperatures close to the boiling point of the solvent. Suitable solvents for the working up are those stated above. Hydrocarbons such as ligroin or petroleum ether are especially useful.

The bisphenols of formula II are known compounds which can be prepared by the methods described in Houben-Weyl, 4th edition, Vol. VI/1c, pages 1028-1030, Thieme-Verlag, Stuttgart 1976. The preparation of the halophosphites is also known, typically by reacting the phosphorus trihalide with suitable 1,3-diols in accordance with the particulars given in Houben-Weyl, 4th edition, Vol. XII/2, pages 45-50, Thieme-Verlag, Stuttgart 1964.

The compounds of formula I have excellent suitability for stabilising organic materials against oxidative, thermal or light-induced degradation. Accordingly, the invention also relates to compositions comprising (a) an organic material susceptible to oxidative, thermal or light-induced degradation and (b) at least one compound of formula I, as well as to the use of compounds of formula I for stabilising such organic materials.

Exemplary of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either $\pi$- or $\sigma$-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals beeing elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethyl/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The organic materials of component (a) to be protected are preferably natural, semi-synthetic or, more particularly, synthetic organic materials. Especially preferred organic materials are thermoplastic polymers, preferably PVC or polyolefins, most preferably polyethylene and polypropylene (PP).

The compositions of this invention conveniently contain the compound of formula I in an amount of 0.01 to 10, typically 0.05 to 5, preferably 0.05 to 3 and, most preferably, 0.05 to 2% by weight. The compositions may contain one ore more components of formula I and the percentages by weight are based on the total amount of said compounds. The computation is based on the total weight of the organic material without the compounds of formula I.

Incorporation in the organic materials can be effected by blending them with, or by applying thereto, the compound of formula I and further optional additives by methods which are commonly used in the art. If the organic materials are polymers, especially synthetic polymers, the incorporation can be effected before or during the fabrication of shaped articles or by applying the dissolved or dispersed compound to the polymer, with or without subsequent evaporation of the solvent. In the case of elastomers, these may also be stabilised as lattices. A further means of blending the compound of formula I into polymers consists in adding said compound before, during or directly after the polymerisation of the corresponding monomers or before crosslinking. The compound of formula I can also be added in encapsulated form (e.g. in waxes, oils or polymers). If the compound of formula I is added before or during polymerisation, it can also act as regulator for the chain length of the polymers (chain terminator).

The compounds of formula I or mixtures thereof can also be added in the form of a masterbatch which contains these compounds to the polymers to be stabilised, typically in a concentration of 2.5 to 25% by weight.

The compounds of formula I may conveniently be incorporated by the following techniques:

as emulsion or dispersion (e.g. to lattices or emulsion polymers), as dry mixture while blending additional components or polymer mixtures by direct addition to the processing apparatus (e.g. extruder, internal mixer and the like)

as solution or melt.

Polymer compositions of this invention can be used in different form and processed to different products, including sheets, filaments, ribbons, moulded articles, profiles or as binders for paints and varnishes, adhesives or putties.

As already mentioned, the organic materials to be protected are preferably natural, semi-synthetic or, more particularly, synthetic polymers. It is especially useful to protect thermoplastic polymers, preferably polyolefins. In this connection, the excellent action of the compounds of formula I as processing stabilisers (heat stabilisers) is to be singled out for special mention. To this end, the compounds of formula I are conveniently added before or during the processing of the polymer.

It is, however, also possible to stabilise other polymers (e.g. elastomers) or lubricants and hydraulic fluids against degradation, such as light-induced and/or thermal oxidative degradation. Examples of elastomers will be found among the above list of possible organic materials.

The suitable lubricants and hydraulic fluids may be based on mineral or synthetic oils or mixtures thereof. The lubricants are known to the skilled person and described in the pertinent technical literature, for example in Dieter Klamann, "Schmierstoffe und verwandte Produkte" (Lubricants and Related Products), Verlag Chemie, Weinheim, 1982, in Schewe-Kobek, "Das Schmiermittel-Taschenbuch" (The Lubricant Handbook), Dr. Alfred Hüthig-Verlag, Heidelberg, 1974) and in "Ullmanns Enzyklopädie der technischen Chemie", (Encyclopedia of Industrial Chemistry), Vol. 13, pages 85-94 (Verlag Chemie, Weinheim, 1977).

The invention further relates to a process for protecting organic material against oxidative, thermal and/or light-induced degradation, which comprises incorporating in, or applying to, said material at least one compound of formula I as stabiliser.

In addition to containing the novel compounds, the compositions of the invention, especially if they contain organic, preferably synthetic, polymers, may contain other conventional additives.

Illustrative examples of such further additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl4-hydroxyanisole, 3,5-di-tert-butyl-4-hydroxyanisole, 3,5-di-tert-butyl-4-hydroxyphenylstearate, bis-(3,5-di-tert-butyl-4-hydroxyphenyl)adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl)disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)-pentane.

1.6. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(3,5-dicyclohexyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert.-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl)propionic acid e.g. N,N'-bis(3,5-di-tert-butyl-4-hydroxyphenylpropionyl)hexamethylenediamine.

N,N'-bis(3,5-di-tert-butyl-4-hydroxyphenylpropionyl)-trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)benztriazole, 2-(3',5'-di-tert-butyl-2'-hydroxyphenyl)-benztriazole, 2-(5'-tert-butyl-2'-hydroxyphenyl)-benztriazole, 2-(2'-hydroxy-5'-(1,1,3,3-tetramethylbutyl)phenyl)-benztriazole, 2-(3',5'-di-tert-butyl-2'-hydroxyphenyl)-5-chlor-benztriazole, 2-(3'-tert-butyl-2'-hydroxy-5'-methylphenyl)-5-chlor-benztriazole, 2-(3'-sec-butyl-5'-tert-butyl-2'-hydroxyphenyl)-benztriazole, 2-(2'-hydroxy-4'-octoxyphenyl)-benztriazole, 2-(3',5'-di-tert-amyl-2'-hydroxyphenyl)-benztriazole, 2-(3',5'-bis-(α,α-dimethylbenzyl)-2'-hydroxyphenyl)-benztriazole, mixture of 2-(3'-tert-butyl-2'-hydroxy-5'-(2-octyloxycarbonylethyl)phenyl)-5-chlor-benztriazole, 2-(3'-tert-butyl-5'-[2-(2-ethylhexyloxy)-carbonylethyl]-2'-hydroxyphenyl)-5-chlor-benztriazole, 2-(3'-tert-butyl-2'-hydroxy-5'-(2-methoxycarbonylethyl)phenyl)-5-chlor-benztriazole, 2-(3'-tert-butyl-2'-hydroxy-5'-(2-methoxycarbonylethyl)phenyl)-benztriazole, 2-(3'-tert-butyl-2'-hydroxy-5'-(2-octyloxycarbonylethyl)phenyl)-benztriazole, 2-(3'-tert-butyl-5'-[2-(2-ethylhexyloxy)carbonylethyl]-2'-hydroxyphenyl)-benztriazole. 2-(3'-dodecyl-2'-hydroxy-5'-methylphenyl)-benztriazole, und 2-(3'-tert-butyl-2'-hydroxy-5'-(2-isooctyloxycarbonylethyl)phenyl-benztriazole, 2,2'-methylene-bis[4-(1,1,3,3-tetramethylbutyl)-6-benztriazole-2-yl-phenol]; the transesterification product of 2-[3'-tert-butyl-5'-(2-methoxycarbonylethyl)-2'-hydroxyphenyl]-2H-benztriazole with polyethylene glycol 300; [R—CH$_2$CH$_2$—COO(CH$_2$)$_3$]$_2$, where R = 3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)-hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetaladipoyl dihydrazide, N,N'-bis(salicyloyl)oxalyl dihydrazide, N,N'-bis(salicyloyl)thiopropionyl dihydrazide.

4. Further phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl)

phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zinc pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. No. 4,325,863 or U.S. Pat. No. 4,338,244.

As further stabilisers it is preferred to use antioxidants, light stabilisers or processing stabilisers. Accordingly, the invention relates in particular to those compositions that contain antioxidants, light stabilisers or processing stabilisers as further stabilisers. Especially preferred compositions are those comprising as further stabilisers phenols, hindered amines (HALS), thiosynergists and/or further phosphorus-containing compounds.

The following Examples illustrate the invention in more detail. In the claims and in the main body of the description parts and percentages are by weight, unless otherwise indicated.

EXAMPLE 1

23.8 g of 1,1-bis(4-hydroxy-3-tert-butylphenyl)cyclohexane and 19.2 ml of triethylamine are dissolved in 360 ml of toluene. With stirring and after cooling to 10° C., 23.4 g of 2-chloro-5,5-dimethyl-1,3-dioxaphosphorinane are slowly added dropwise to this solution. The mixture is then kept for 1 h at 10° C. with stirring. Afterwards triethylamine hydrochloride is removed by filtration, the filtrate is concentrated by evaporation and the residue is dissolved in 100 ml of ligroin at 100° C. After further filtration and cooling to 5° C., the product is filtered with suction and dried over diphosphorus pentoxide under reduced pressure, giving 31.65 g of the compound of formula

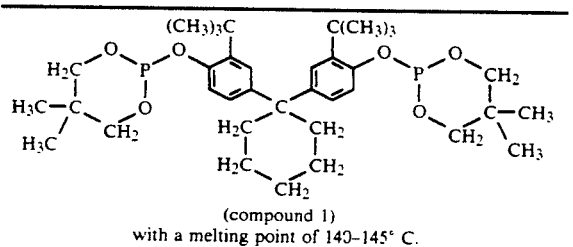

(compound 1) with a melting point of 140–145° C.

| Elemental analysis: | % C | % H | % P |
|---|---|---|---|
| calcd.: | 67.06 | 8.44 | 9.61 |
| found: | 67.03 | 8.40 | 9.56. |

EXAMPLES 2–10

Compounds 2 to 5 and 7 to 10 are prepared according to the method described in Example 1. The preparation of compound 6 is in accordance with the particulars of Example 1, except that butyl lithium is used as base in stoichiometric proportion to the phenolic OH groups. Structural formulae and characterisation of the compounds obtained are summarised in Table 1.

TABLE 1

| No. | Compound | Characterisation | | |
|---|---|---|---|---|
| | Characterisation of the compounds 2 to 10 | | | |
| 2 | [structure] | Yield: 63% mp: 174–178° C. | | |
| | | % C | % H | % P |
| | | calcd.: 65.29 | 7.88 | 10.52 |
| | | found: 65.4 | 7.91 | 10.2 |

TABLE 1-continued

Characterisation of the compounds 2 to 10

| No. | Compound | Characterisation |
|---|---|---|
| 3 | [structure] | Yield: 72%<br>mp: 59–62° C.<br>　　　　% C　% H　% P<br>calcd.: 69.98　8.1　8.9<br>found: 69.58　8.24　8.46 |
| 4 | [structure] | Yield: 64%<br>mp: 202–204° C.<br>　　　　% C　% H<br>calcd.: 67.84　8.69<br>found: 67.73　8.83 |
| 5 | [structure] | Yield: 29%<br>mp: 102–109° C.<br>　　　　% C　% H<br>calcd.: 70.38　9.50<br>found: 70.44　9.47 |
| 6 | [structure] | Yield: 89%<br>mp: 261–265° C.<br>　　　　% C　% H　% P<br>calcd.: 69.81　9.32　8.18<br>found: 69.64　9.39　8.13 |
| 7 | [structure] | Yield: 90%<br>resin:<br>$^{31}$P-NMR (CDCl$_3$):<br>δ(P) = 114.5 ppm |
| 8 | [structure] | Yield: 93%<br>resin:<br>$^{31}$P-NMR (CDCl$_3$):<br>δ(P) = 114.6 ppm |

TABLE 1-continued

Characterisation of the compounds 2 to 10

| No. | Compound | Characterisation |
|---|---|---|
| 9 | (structure) | Yield: 95%<br>resin:<br>$^{31}$P-NMR (CDCl$_3$):<br>$\delta$(P) = 115.7 ppm |
| 10 | (structure) | Yield: 48%<br>mp: 221-224° C.<br>　　　% C　　% H<br>calcd.: 66.65　8.31<br>found: 66.84　8.25 |

EXAMPLE 11

Stabilisation of multiple-extruded polypropylene 1.3 kg of polypropylene powder (Propathene ® HF 24, Moplen ® FL S20, Profax ® 6501), having a melt index indicated in Table 2 measured at 230°/2.16 kg, are blended with 0.05% of Irganox ® 1010 (pentaerythrityl tetrakis-[3-(3,5-di-tert-butyl-4-hydroxyphenyl)propionate), 0.05% of calcium stearate, an amount of hydrotalcite-like compound indicated in Table 2 [DHT 4A ®, Kyowa Chemical Industry Co., Ltd., Mg$_{4.5}$Al$_2$(OH)$_{13}$CO$_3$•3,5 H$_2$O] and 0.05% of the compound of Table 1. This blend is then extruded in an extruder having a cylinder diameter of 20 mm and a length of 400 mm at 100 rpm, the 3 heating zones being adjusted to the following temperatures: 260° C., 270° C., 280° C. The extrudate is cooled by drawing it through a water bath and then granulated. This granulate is repeatedly extruded. The melt index is measured online during processing and corresponds to a value which would be conventionally measured at 230° C./2.16 kg/10 min. A substantial increase in the melt index denotes pronounced chain degradation, i.e. poor stabilisation. The results are shown in Table 2.

TABLE 2

Melt index of polypropylene before extrusion and after 3 extrusions

| Hydrotalcite-like compound DHT4A ® (ppm) | Melt index before 1st extrusion | Compound of Table 1 | Melt index after 3rd extrusion |
|---|---|---|---|
| 0 | 3.4$^{a)}$ | — | 23.0 |
| 0 | 3.4$^{a)}$ | 1 | 6.2 |
| 0 | 3.4$^{a)}$ | 3 | 6.1 |
| 300 | 1.8$^{b)}$ | — | 12.0 |
| 300 | 1.8$^{b)}$ | 2 | 3.0 |
| 300 | 1.8$^{b)}$ | 4 | 2.7 |
| 300 | 3.2$^{c)}$ | — | 18.9 |
| 300 | 3.2$^{c)}$ | 1 | 5.6 |
| 300 | 3.2$^{c)}$ | 5 | 5.2 |
| 300 | 3.2$^{c)}$ | 6 | 5.5 |
| 300 | 3.2$^{c)}$ | 9 | 6.3 |
| 300 | 3.2$^{c)}$ | 10 | 5.2 |

$^{a)}$Propathene ® HF 24
$^{b)}$Moplen ® FL S20, prestabilised with 150 ppm of Irganox ® 1076
$^{c)}$Profax ® 6501, prestabilised with 250 ppm of Irganox ® 1076
Irganox ® 1076 = n-octadecyl 3-[3,5-di-tert-butyl-4-hydroxyphenyl]propionate

EXAMPLE 12

Test for stabilising polyacetal against yellowing during processing 100 parts of polyacetal powder (Hostaform ® C) are blended with 0.3 part of calcium stearate and with the amounts of Irganox ® 1010 (pentaerythrityl tetrakis-[3-(3,5-di-tert-butyl-4-hydroxyphenyl)propionate) indicated in Table 3 and compound 1 of Table 1. The blend is then kneaded in a Brabender plastograph for 7 minutes at 190° C./30 rpm. The kneading stock is thereafter compressed to 1 mm boards. The Yellowness Index (YI) of the boards is taken as reference value for the stabilising action (measured according to ASTM D-1925-70). Low YI values denote insignificant, and high YI values strong, yellowing. The lesser the yellowing the more effective the stabiliser. The results are reported in Table 3.

TABLE 3

Stabilisation of polyacetal against yellowing during processing

| Irganox 1010 (parts per 100 parts of polyacetal) | Compound 1 (Table 1) (parts per 100 parts of polyacetal) | Yellowness Index (YI) |
|---|---|---|
| 0.3 | — | 7.25 |
| — | 0.3 | 2.25 |
| 0.25 | 0.05 | 3.3 |

What is claimed is:

1. A compound of formula I

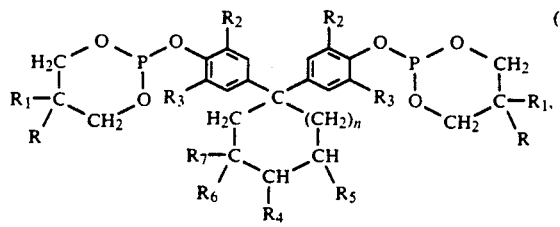

wherein
n is 0, 1 or 2,
R and $R_1$ are each independently of the other $C_1$-$C_4$alkyl or, when taken together, are a 2,3-dehydropentamethylene radical,
$R_2$ is $C_1$-$C_4$alkyl or $C_5$-$C_6$cycloalkyl, and
$R_3$ is hydrogen, $C_1$-$C_4$alkyl or $C_5$-$C_6$cycloalkyl,
$R_4$, $R_5$, $R_6$ and $R_7$, if n=1, are each independently of one another hydrogen or $C_1$-$C_4$alkyl, or, if n=0 and if n=2, are hydrogen.

2. A compound according to claim 1, wherein n is 1 or 2.

3. A compound according to claim 1, wherein $R_2$ is $C_1$-$C_4$alkyl or $C_5$-$C_6$cycloalkyl and $R_3$ is hydrogen, $C_1$-$C_4$alkyl or cyclohexyl.

4. A compound according to claim 1, which n=1.

5. A compound according to claim 1, wherein n=1, $R_4$ is hydrogen and $R_5$, $R_6$ and $R_7$ are each independently of one another hydrogen or methyl.

6. A compound according to claim 1, wherein $R_2$ is methyl, butyl or cyclohexyl and $R_3$ is hydrogen, methyl, butyl or cyclohexyl.

7. A compound according to claim 1, wherein $R_2$ is methyl or tert-butyl and $R_3$ is hydrogen, methyl or tert-butyl.

8. A compound according to claim 1, wherein $R_5$, $R_6$ and $R_7$ are hydrogen and $R_4$ is hydrogen or tert-butyl.

9. A compound according to claim 1, wherein $R_4$, $R_5$, $R_6$ and $R_7$ are hydrogen.

10. A compound according to claim 1, wherein R and $R_1$ are each independently of the other methyl or butyl or, when taken together, are a 2,3-dehydropentamethylene radical.

11. A composition comprising (a) an organic material susceptible to oxidative, thermal or light-induced degradation and (b) at least one compound of formula I according to claim 1.

12. A composition according to claim 11, wherein component (a) is a natural, semi-synthetic or synthetic polymer.

13. A composition according to claim 11, wherein component (a) is a thermoplastic polymer.

14. A composition according to claim 11, wherein component (a) is a polyolefin or a polyvinyl chloride.

15. A composition according to claim 11, wherein component (a) is polyethylene or polypropylene.

16. A composition according to claim 11, comprising in addition to components (a) and (b) an antioxidant, a light stabiliser or a processing stabiliser.

17. A method of protecting organic material against oxidative, thermal or light-induced degradation, which comprises incorporating in, or applying to, said material at least one compound of formula I as stabiliser.

* * * * *